(12) United States Patent
Bartholomaeus et al.

(10) Patent No.: US 6,451,350 B1
(45) Date of Patent: Sep. 17, 2002

(54) CONTROLLED RELEASE TRAMADOL PREPARATION WITH A STORAGE-STABLE RELEASE PROFILE AND PROCESS FOR THEIR PRODUCTION

(75) Inventors: Johannes Heinrich Bartholomaeus, Aachen; Iris Ziegler, Rott-Roetgen, both of (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 09/484,017

(22) Filed: Jan. 18, 2000

(30) Foreign Application Priority Data

Jan. 18, 1999 (DE) .......................... 199 01 686

(51) Int. Cl.[7] .............. A61K 9/16; A61K 9/14; A61K 9/50
(52) U.S. Cl. ............ 424/490; 424/489; 424/494; 424/495
(58) Field of Search ............... 424/489, 490, 424/494, 495

(56) References Cited

U.S. PATENT DOCUMENTS 5,645,858 A * 7/1997 Kotwal et al. .............. 424/495
6,077,533 A * 6/2000 Oshlack et al. ............. 424/461

FOREIGN PATENT DOCUMENTS

| DE | 196 30 035 | 1/1998 |
|----|------------|--------|
| EP | 0 548 448  | 6/1993 |
| EP | 0 630 646  | 12/1994 |

OTHER PUBLICATIONS

Wesseling et al., European Journal of Pharmaceutics and Biopharmaceutics, 47 (1999) 33–38, "Drug Release from beads coated with an aqueous colloidal ethylcellulose dispersion, Aquacoat®, or an organic ethylcellulose solution".

Nesbitt et al., Journal of Controlled Release 32 (1994) Nov., No. 1, 71–77, "Effect of substrate on mass release from ethylcellulose latex coated pellets".

* cited by examiner

*Primary Examiner*—Thurman K. Page
*Assistant Examiner*—S. Tran
(74) *Attorney, Agent, or Firm*—Crowell & Moring LLP

(57) ABSTRACT

A process for producing an oral, controlled release preparation of tramadol or a physiologically compatible tramadol salt having a storage stable active substance release profile by coating the active substance preparation with an aqueous ethylcellulose dispersion which contains at least one physiologically compatible, lipophilic diester of a $C_6$–$C_{40}$ aliphatic or aromatic dicarboxylic acid and a $C_1$–$C_8$ aliphatic alcohol as plasticizer, and, during coating, drying the coating at conventional temperatures, with the result that a storage stable active substance release profile is obtained even without subsequent heat treatment. Optionally, in order to increase the active substance release profile without impairing the storage stability of the preparation, a heat treatment may be performed at temperatures of >35° C. until a desired, increased active substance release profile is achieved.

26 Claims, 11 Drawing Sheets

CONTROLLED RELEASE TRAMADOL PREPARATION WITH A STORAGE-STABLE RELEASE PROFILE AND PROCESS FOR THEIR PRODUCTION

BACKGROUND OF THE INVENTION

The present invention relates to preferably multiparticulate, oral tramadol preparations, having a controlled active substance release profile which is established in a storage-stable manner by an ethylcellulose coating containing plasticizer even without heat treatment.

Multiparticulate, controlled release tramadol preparations having a controlled release coating of ethylcellulose are known in the prior art. DE-A-196 30 035 accordingly describes multiparticulate tramadol preparations in the form of pellets which are provided with a controlled release coating of ethylcellulose. To this end, accretion pellets are coated with one or more ethylcellulose membrane layers which are applied from solutions in organic solvents. This production method has the disadvantage that the organic solvents must be recovered on environmental grounds, thus rendering this process somewhat costly. It is moreover disadvantageous to use organic solvents in the production of pharmaceuticals.

Where controlled release coatings of aqueous ethylcellulose dispersions are applied onto substrates, it is generally recognized by experts that, once produced, such coatings do not usually provide storage-stable active substance release profiles. Such ethylcellulose coatings are indeed known to have a tendency to "post-filming", i.e. active substance release is increasingly delayed over storage. In order to overcome this problem, elaborate heat treatment processes at elevated temperature and optionally defined atmospheric humidity are recommended in the prior art in order to achieve a storage-stable release profile within days rather than after several months' storage (EP-A-0 548 448, EP-A-0 630 646).

According to the teaching of U.S. Pat. No. 5,645,858, it has also been proposed to provide a multiparticulate tramadol preparation in the form of accretion pellets with two or more controlled release coatings of ethylcellulose and to subject the resultant coated accretion pellets of the active substance to a heat treatment process for one day at elevated temperature in order to achieve a stable release profile.

Known methods for producing controlled release coatings from aqueous ethylcellulose. dispersions thus have the disadvantage that a storage-stable active substance release profile of tramadol or tramadol hydrochloride is achieved only by elaborate heat treatment processes or only by multilayer application in combination with a heat treatment process.

SUMMARY OF THE INVENTION

The object of the present invention was accordingly to provide oral tramadol preparations having a controlled release ethylcellulose coating which, despite being applied from an aqueous ethylcellulose, dispersion, has a largely storage-stable active substance release profile immediately after the production thereof, and which may optionally, if desired, be still further increased without affecting storage stability.

This is achieved according to the invention by the process of the invention, in accordance with which a preferably multiparticulate, oral, controlled release tramadol preparation or a preparation of a physiologically compatible salt of tramadol having a storage stable active substance release profile is produced. To this end, the preferably multiparticulate active substance preparation is coated with an aqueous ethylcellulose dispersion which contains at least one physiologically compatible, lipophilic diester of a $C_6$–$C_{40}$ aliphatic or aromatic dicarboxylic acid and a $C_1$–$C_8$ aliphatic alcohol as plasticizer, and the coating is dried at conventional temperatures.

The controlled release tramadol preparations produced in this manner surprisingly exhibit a storage stable active substance release profile immediately after the production thereof, without any heat treatment subsequent to the conventional drying being necessary. The controlled release tramadol preparations produced according to the invention exhibit a so-called coalesced ethylcellulose coating, in which the discrete ethylcellulose particles have coalesced to form a coating.

The controlled release active substance preparations according to the invention furthermore have the unexpected advantage that the active substance release profile may be increased as desired without the storage stability of the increased active substance release profile being impaired. This is achieved by heat treating the controlled release active substance preparations after production thereof at temperatures of >35° C. until the selected, increased release profile is achieved.

Tramadol or preferably a physiologically compatible salt of tramadol, such as tramadol hydrochloride, is used for the process according to the invention in the form of tablets, microtablets, granules, crystals, pellets, such as extrusion or accretion pellets preferably having a size of 0.3 to 2.5 mm. The production of such multiparticulate substrates is known to persons skilled in the art.

The controlled release coatings are produced by using aqueous ethylcellulose dispersions having a concentration of water-insoluble ethylcellulose of 3 to 35 wt. %, preferably of 10 to 25 wt. %. The aqueous ethylcellulose. dispersions which are used as the coating material contain at least one physiologically compatible lipophilic diester of a $C_6$–$C_{40}$, preferably $C_6$–$C_{30}$, particularly preferably $C_{10}$–$C_{16}$ aliphatic or aromatic dicarboxylic acid and a $C_1$–$C_8$, preferably $C_2$–$C_6$, particularly preferably $C_2$–$C_5$ aliphatic alcohol as a plasticizer. The plasticizers used are preferably dibutyl phthalate, diethyl phthalate, dibutyl sebacate or diethyl sebacate, particularly preferably dibutyl sebacate. The quantity of plasticizer is from 5 to 50 wt. %, preferably 10 to 40 wt. %, particularly preferably 10 to 30 wt. %, relative to ethylcellulose. Especially preferred controlled release coatings are those prepared from ethylcellulose containing 10 to 30 wt. % dibutyl sebacate, relative to the ethylcellulose.

The aqueous ethylcellulose dispersions used may be commercial products such as, for example, Aquacoat™ or Surelease™. Such dispersions, such as for example Surelease, may already contain the necessary plasticizer. It is, however, also possible to incorporate the plasticizers into the aqueous ethylcellulose dispersion, preferably with the assistance of surfactants or emulsifiers, such as for example polysorbate 80 (Tween 80™). It is particularly preferred to use an aqueous ethylcellulose dispersion which already contains the plasticizer as a component during the production of the ethylcellulose dispersion, such as the commercial product Surelease E-7-7050™.

The release profiles obtained immediately after production may be adjusted by methods known to persons skilled in the art, such as for example by varying the particular thickness of the coating or by addition of further auxiliary substances as coating constituents. Pigments, such as iron oxides, titanium dioxide, lubricants, such as talcum, Aerosil, glycerol monostearate, hydrophilic pore-formers such as lactose, polyethylene glycol, mannitol and/or water-soluble polymers, such as hydroxypropylmethylcellulose, polyvidone, may be considered for this purpose. It is also possible by blending with other coating dispersions, such as for example Eudragit™ RS 30D, RL 30D, NE 30D, or dispersions of film-formers resistant to gastric juices, such as for example Endragit L 30D, to control the release of the active substance such that a delay on the order of at least 4 hours up to 24 hours is achieved.

The controlled release coating of ethylcellulose is produced by coating the active substance substrates, once produced, with the aqueous dispersion by spraying, preferably using the fluidized bed process, and simultaneously drying at conventional temperatures. Desired product temperatures in this process are at least 35° C., preferably 35° C. to 80° C., particularly preferably 40° C. to 45° C., which are established using feed air at a temperature of at least 50° C., preferably of 55° C. to 70° C.

In the event that the storage stable release profile of the active substance obtained immediately after production is subsequently to be changed, it is possible after drying to expose the controlled release active substance preparations to heat treatment at temperatures of >35° C. until the desired increase in release of the active substance is achieved. By measuring the particular active substance release profile as a function of the duration of the heat treatment process at a specific temperature, persons skilled in the art are able to determine the correlation between release profile and heat treatment conditions by means of simple tests. It is thus straightforwardly possible to establish an appropriate active substance release profile at any time.

The present invention accordingly also provides oral, preferably multiparticulate, controlled release preparations of tramadol or a physiologically compatible salt of tramadol having a storage stable active substance release profile. The controlled release tramadol or tramadol salt preparations according to the invention are characterized by the active substance preparation being provided with a coalesced ethylcellulose coating, which has been obtained by coating the preferably multiparticulate active substance preparation with an aqueous ethylcellulose dispersion containing a plasticizer which is comprised of a lipophilic diester of a $C_6$–$C_{40}$ aliphatic or aromatic dicarboxylic acid and a $C_1$–$C_8$ aliphatic alcohol, and which provides a storage stable active substance release profile after only drying the coating at conventional temperature. The active substance release profile may be increased by subsequent heat treatment at temperatures of >35° C. without affecting storage stability.

In order to protect the very readily water-soluble tramadol or tramadol salt, such as tramadol hydrochloride, during coating with the aqueous ethylcellulose dispersion, it may be advantageous to apply a protective coating to the active substance substrate before application of the controlled release coating. The protective coating is preferably applied for isolation purposes in a quantity of 1 to 10 wt. %, preferably of 2.5 to 5 wt. %, relative to the quantity of the active substance substrate to be coated. This results in no substantial reduction in the application rate required for controlled release purposes, but avoids dissolution of the water-soluble active substance during coating with ethylcellulose and prevents the active substance from penetrating the controlled release film.

Aqueous solutions of water-soluble polymers, such as for example hydroxypropylmethylcellulose or hydroxypropylcellulose, poylvidone with or without further auxiliary substances, such as for example talcum, or lipophilic substances applied by melt coating or from organic solutions, such as for example fatty alcohols, fatty acids, fats, waxes, glycerol monostearate, glycerol behenate types may be used as a protective coating material.

External coatings over the controlled release substrates are generally applied in order to prevent adhesion of the substrates during storage. The external coatings may, however, also be functional coatings which provide additional protection, for example against elevated atmospheric humidity or against the penetration of gastric acid into the substrate. The quantity of the external coating is determined in accordance with its function and ranges from ≦1 wt. % to provide protection against sticking up to 30 wt. % to increase resistance to gastric juices.

DETAILED DESCRIPTION OF PREFERRED EMBODIMENTS

Figure 1:
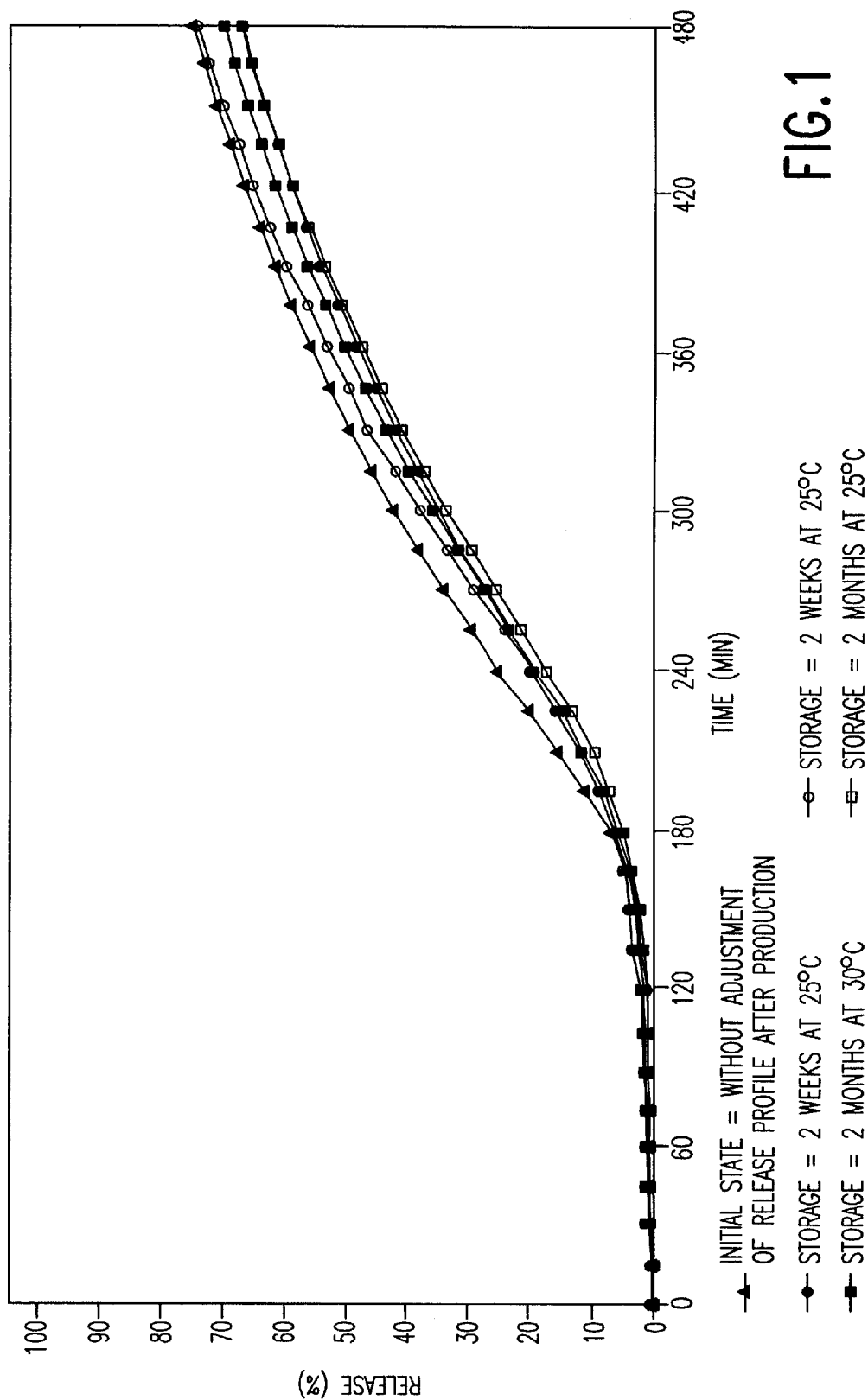
FIG. 1 is a graph showing the storage stability of tramadol release from pellets coated with 11% of a coating according to the invention without adjustment of the release profile after coating.
Figure 2:
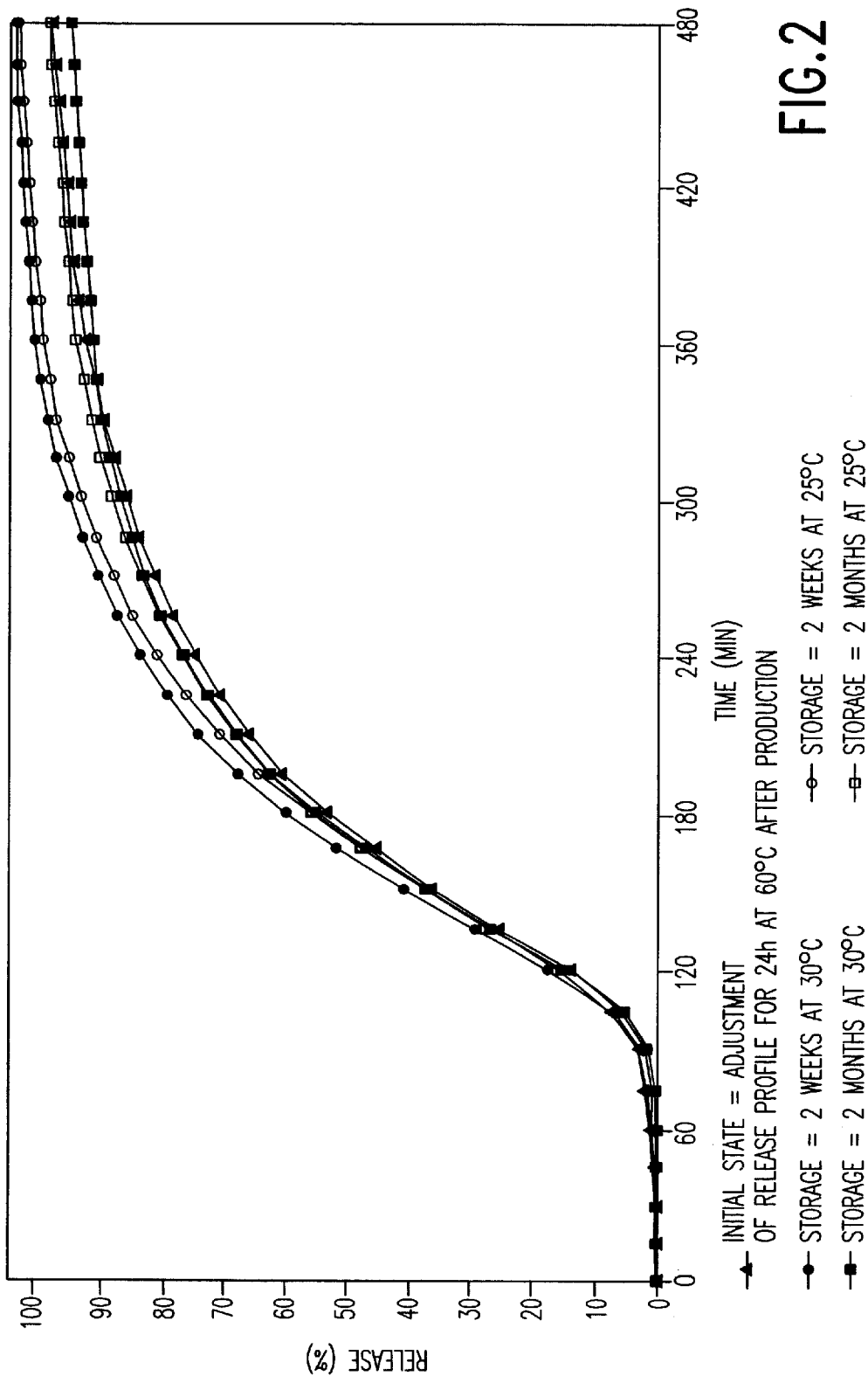
FIG. 2 is a graph showing the storage stability of tramadol release from pellets coated with 11% of a coating according to the invention after adjustment of the release profile for 24 hours at 60° C.
Figure 3:
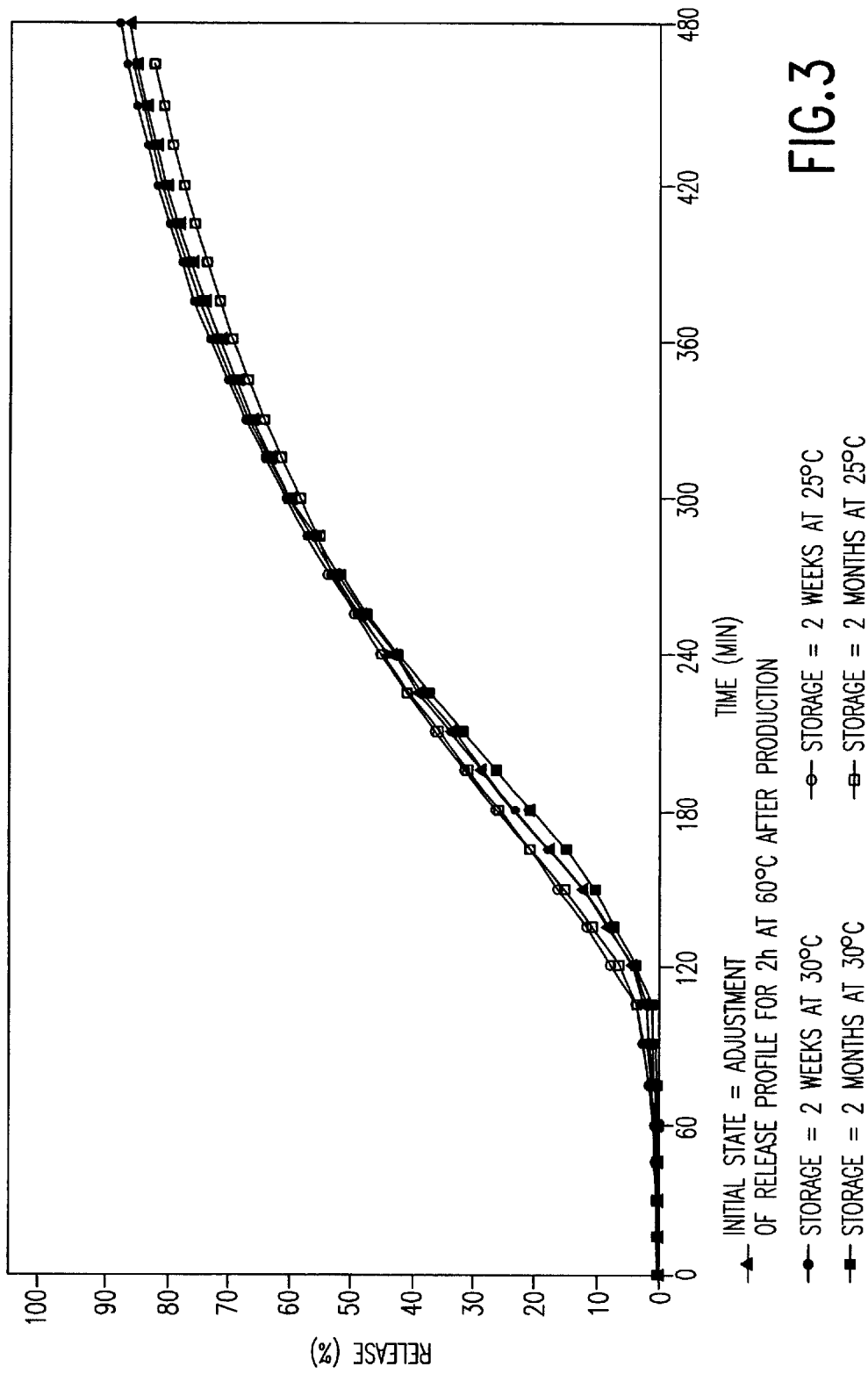
FIG. 3 is a graph showing the storage stability of tramadol release from pellets coated with 11% of a coating according to the invention after adjustment of the release profile for 2 hours at 60° C.

As FIG. 1 to FIG. 3 show, all three release profiles for tramadol HCl remain unchanged under conventional storage conditions of 25° C. to 30° C. over the entire period of storage and at both storage temperatures. Storage stability is measured according to USP 23, pages 1959 et seq. "[1196]

The stability testing of new drug substances and products—The tripartite guideline".

Despite having identical film thickness and film composition, in the combined dissolution test comprising 2 hours in gastric juice, pH 1.2, and 8 hours in intestinal juice, pH 7.2, they exhibit completely different initial release rates. While the film without additional treatment after production exhibits the greatest delay with a release of approx. 75% in 8 hours, the same film, once heat treated for 24 hours at 60° C., releases 100% after only 5 hours. Heat treatment for 2 hours at 60° C. results in approx. 90% tramadol release in 8 hours. These various release profiles show that appropriate, storage stable tramadol release may be achieved with coatings of coalesced ethylcellulose with the appropriate plasticizers, which release may occur, as required, both immediately after production or also after storage of the tramadol preparations coated with the coating according to the invention. This provides the major advantage for the large scale industrial production of the preparations that any batches with an excessively slow release profile may be worked up at any time. The release profile may also subsequently be adjusted to the required release profile by purposeful post-treatment at, for example, 60° C., without impairing the storage stability of the preparation.

Figure 4:
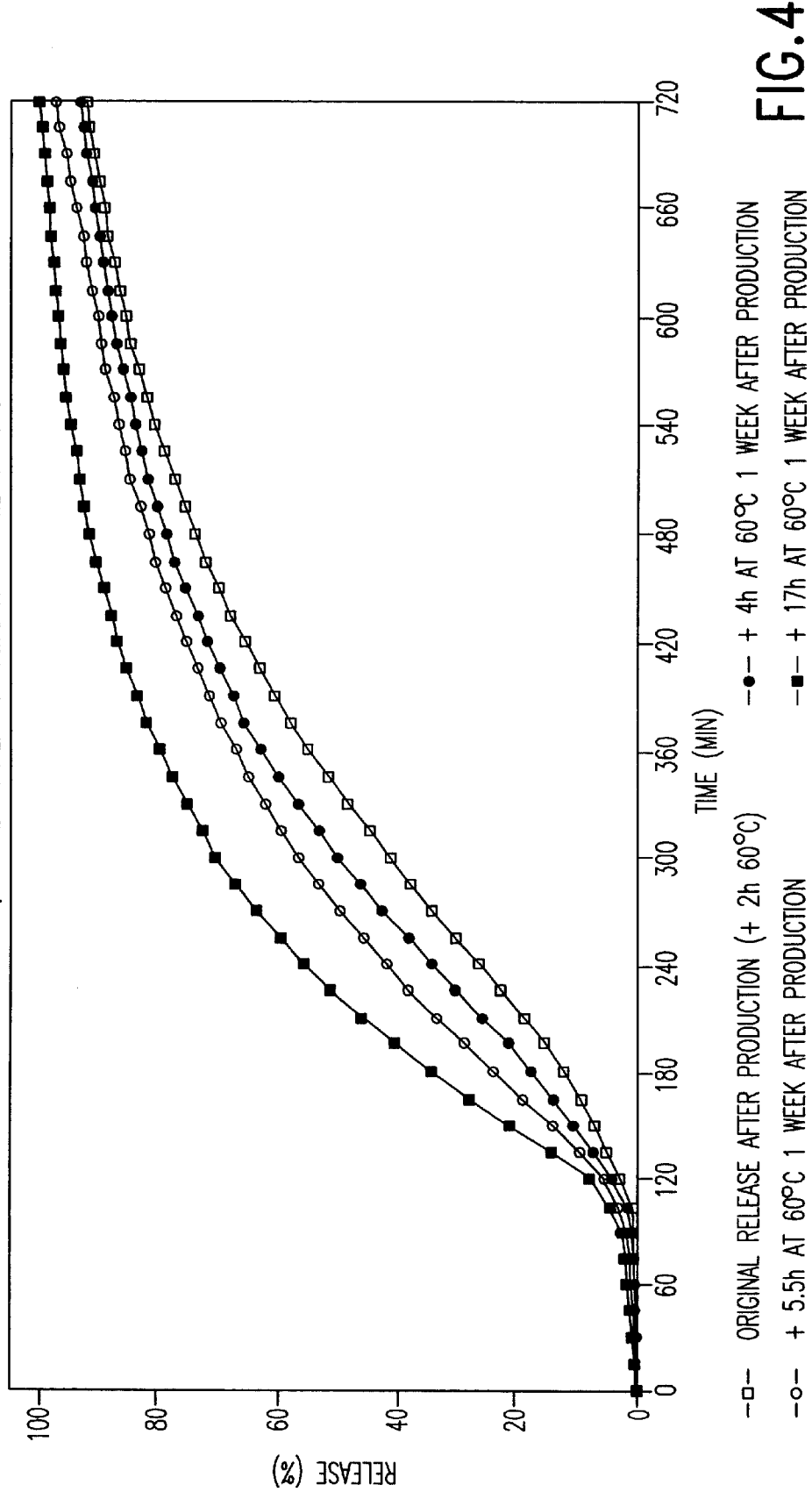
FIG. 4 is a graph showing the adjustment of tramadol release from pellets coated with a coating according to the invention by subsequent adjustment treatment at 60° C.

FIG. 4 shows how the release profile of tramadol HCl pellets with the coating according to the invention having a relatively slow release immediately after production of less than 45% after 300 minutes may be modified in stages towards faster release up to 70% in 300 minutes.

In addition to the standard dissolution test of 2 hours in gastric juice+6 hours in intestinal juice, the controlled released tramadol HCl preparations according to the invention were also tested for 8 hours with a pH gradient of pH 1.2 to pH 7.2, for 8 hours in artificial intestinal juice, pH 7.2, with 100 mM of NaCl (250 mM $KH_2PO_4$+100 mM NaCl), 8 hours in artificial intestinal juice, pH 6.8 (220 mM KCl+30 mM $KH_2PO_4$), 8 hours in artificial gastric juice, pH 1.2, 8 hours in buffer, pH 4.6 (100 mM $NaC_2H_3O_2$+50 mM NaCl) and 8 hours in artificial intestinal juice, pH 6.8 with 5 mM of Na taurocholate (220 mM KCl+30 mM $KH_2PO_4$). Unless otherwise stated, release was tested in baskets at a rotational speed of 100 $m^{-1}$. Other rotational speeds were, however, also tested in order to reveal the influence of mechanical stress on release.

Figure 5:
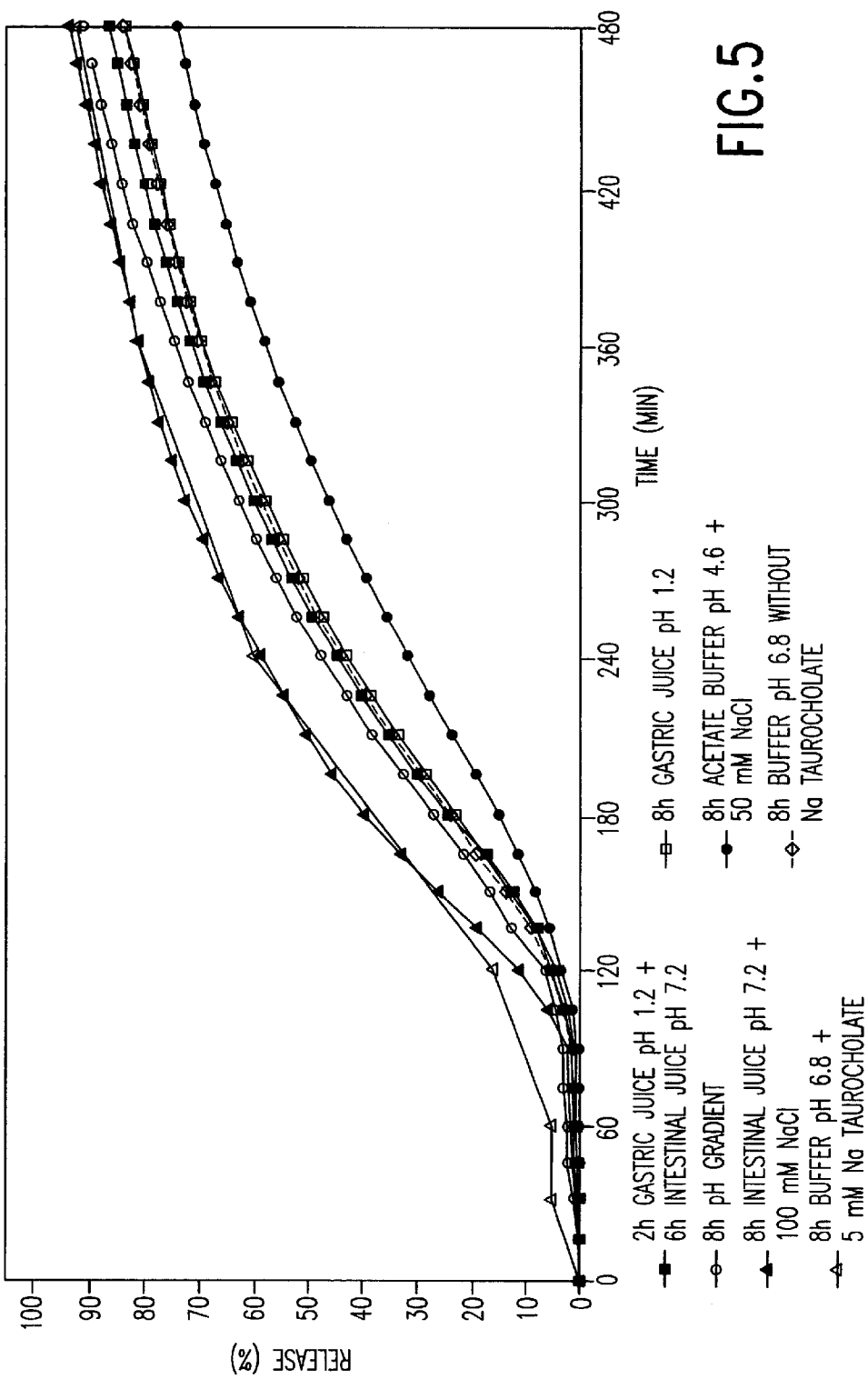
FIG. 5 is a graph showing the influence of the composition of the dissolution medium on tramadol release from pellets coated with a coating according to the invention.
Figure 6:
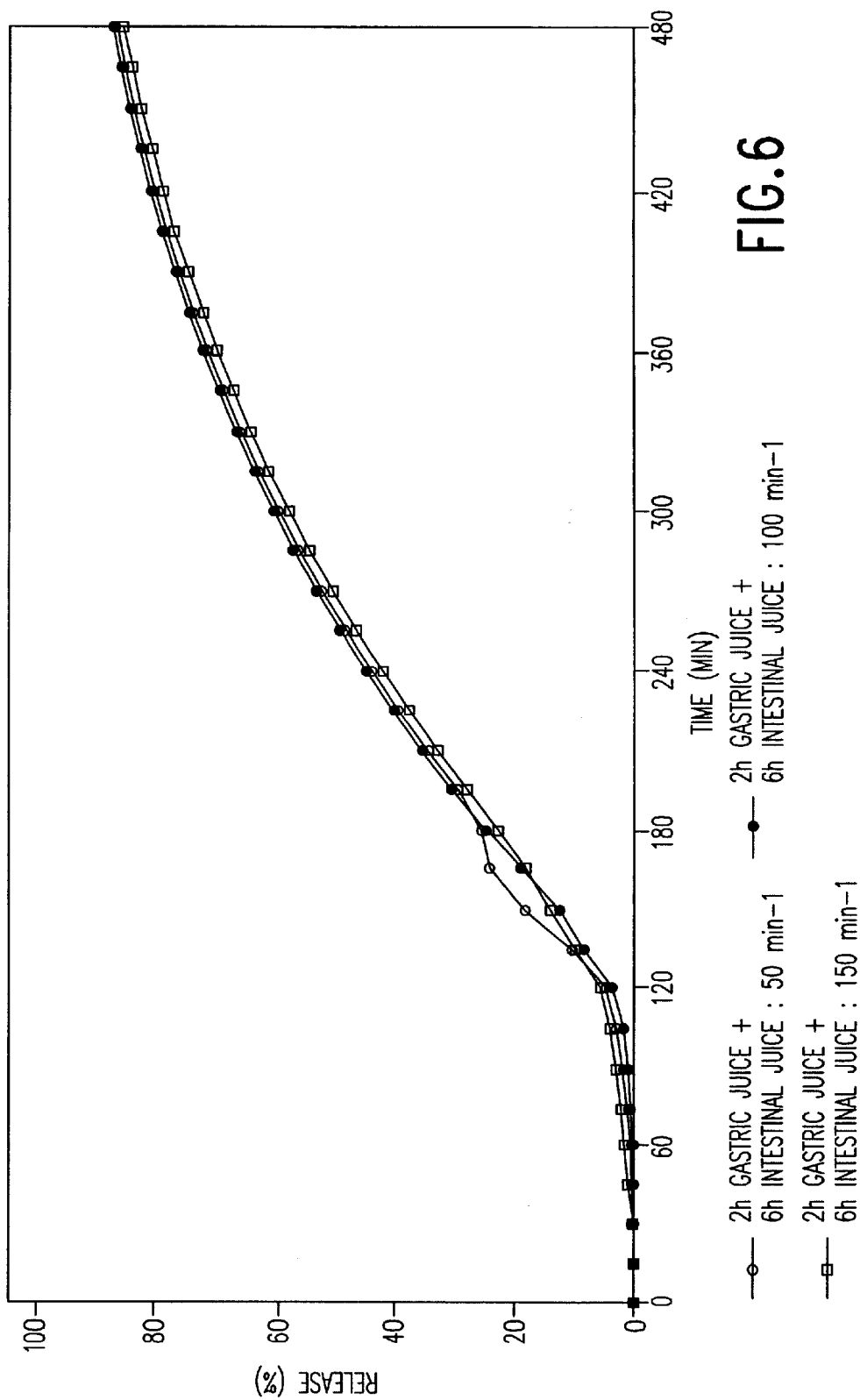
FIG. 6 is a graph showing the influence of basket rotational speed on tramadol release from pellets coated with a coating according to the invention.

As can be seen from FIG. 5 and FIG. 6, neither the composition of the release medium with regard to molarity, pH value or type of ion, nor the level of mechanical stress to which the pellets were exposed had any great influence upon tramadol release from pellets coated with the coating according to the invention. This accordingly confirms robust release behavior of the preparations according to the invention with regard to in vitro testing, such that reliable release may also be expected in vivo.

EXAMPLES

In vitro release of tramadol was determined by the dissolution test to Ph. Eur. using the basket method at a rotational speed of 100 $m^{-1}$. Unless otherwise stated, the preparation was initially tested for 2 hours in artificial gastric juice, pH 1.2, and then for a further 6 hours in artificial intestinal juice, pH 7.2. The quantity of tramadol in solution at each particular measurement time was determined spectrophotometrically and stated as a percentage of the total dose of tramadol hydrochloride. The stated release values and curves are the mean from n=3 tests.

Example 1

Tramadol HCl pellets having an active substance content of 70 wt. % were produced by aqueous granulation with microcrystalline cellulose and hydroxypropylcellulose with a low degree of substitution, extrusion and subsequent spheronisation. The dried pellets having a screened size of 800–1250 μm were then coated by the fluidized bed method at a feed air temperature of 60° C. initially with 3 wt. % of protective coating of hydroxypropylmethylcellulose, PEG 400 and talcum and then provided with a controlled release coating of 11 wt. %, relative to the weight of the pellets.

The composition of the aqueous dispersion for producing a protective coating on 5 kg of pellets was:

| | |
|---|---|
| Hydroxypropylmethylcellulose (Pharmacoat 603/ShinEtsu) | 104.0 g |
| PEG 400 | 12.0 g |
| Micronized talcum | 35.0 g |
| Purified water | 2160.0 g |
| Total: | 2311.0 g |

The composition of the aqueous coating composition for coating 5 kg of pellets provided with protective coating was:

| | |
|---|---|
| Surelease E-7-7050 (aqueous ethylcellulose dispersion; Colorcon) | 2115.0 g |
| Purified water | 1323.0 g |
| Total: | 3438.0 g |

Figure 7:
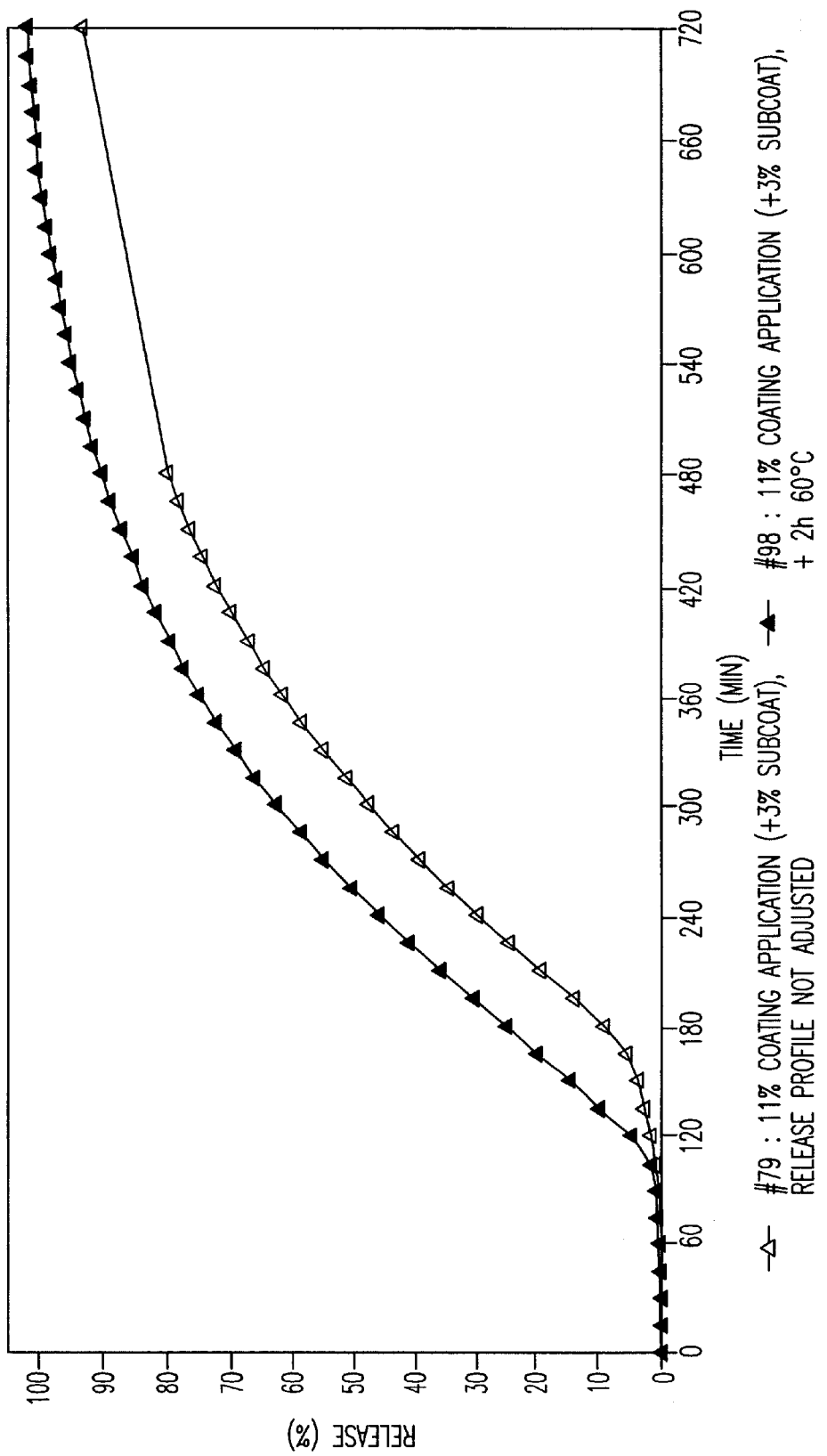
FIG. 7 is a graph showing tramadol release from pellets provided with an 11% Surelease E-7-7050 coating and a 3% subcoat.

The solids content of the dispersion was 16 wt. %. Once the pellets had been coated, they were either not heat treated, or the active substance release was adjusted for 2 hours at 60° C. 163 mg of pellets, corresponding to a dose of 100 mg of tramadol hydrochloride, were packaged in size 1 capsules and active substance release determined as stated above. The stated release values are the mean from n=6 tests (FIG. 7).

| Time in min | Proportion released in % | Proportion released in % after 6 months' storage at 25° C. | Proportion released in % after 6 months' storage at 30° C. | Proportion released in % after treatment for 2 h at 60° C. | Proportion released in % after 6 months' storage at 25° C. | Proportion released in % after 6 months' storage at 30° C. |
|---|---|---|---|---|---|---|
| 120 | 1 | 1 | 1 | 5 | 4 | 5 |
| 240 | 29 | 26 | 27 | 46 | 45 | 48 |
| 360 | 61 | 61 | 60 | 75 | 70 | 74 |
| 480 | 80 | 79 | 78 | 91 | 86 | 90 |
| 600 | 94 | 95 | 94 | 99 | 98 | 100 |

Example 2

Tramadol HCl pellets having an active substance content of 55 wt. % were produced by aqueous granulation with microcrystalline cellulose and hydroxypropylcellulose with a low degree of substitution, extrusion and subsequent spheronisation. The dried pellets having a screened size of 800–1250 μm were then coated by the fluidized bed method at a feed air temperature of 60° C. with a total coating weight of 8 wt. %, relative to the starting weight of the pellets.

The composition of the aqueous dispersion for coating 300 g of pellets was:

| | |
|---|---|
| Aquacoat ECD 30 (aqueous ethylcellulose dispersion) | 53.0 g |
| Dibutyl sebacate | 4.8 g |
| Talcum (micronized) | 3.2 g |
| Polysorbate 80 | 0.02 g |
| Silicon emulsion | 0.02 g |
| Purified water | 65.0 g |
| Total: | 126.0 g |

Figure 8:
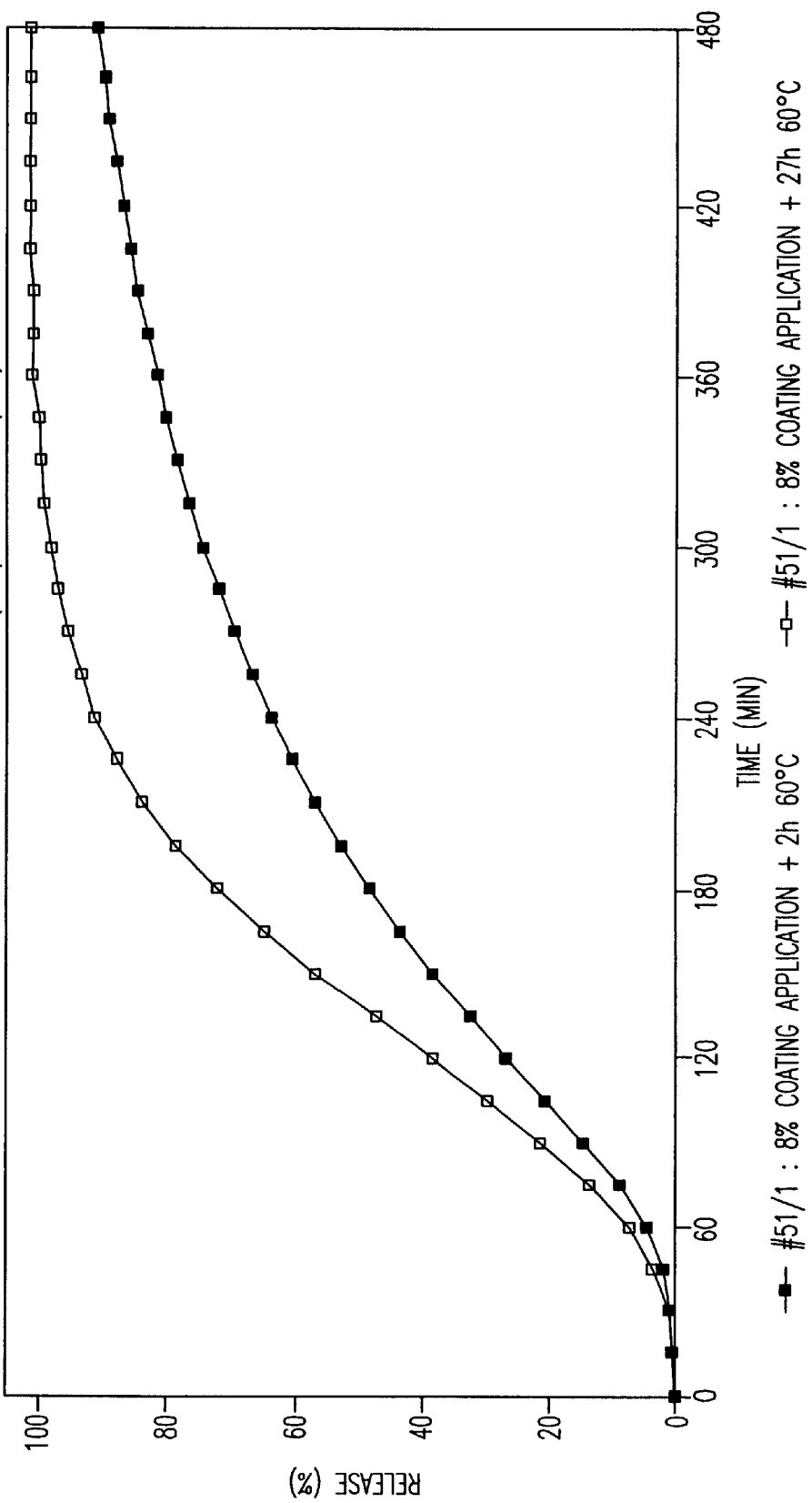
FIG. 8 is a graph showing tramadol release from pellets coated with an Aquacoat ECD 30, dibutyl sebacate (30%) and talcum (20%) coating according to the invention.

The solids content of the dispersion was 19 wt. %. Once the pellets had been coated, active substance release was adjusted for 2 or 27 hours at 60° C. 196 mg of pellets, corresponding to a dose of 100 mg of tramadol hydrochloride, were packaged in size 1 capsules and active substance release determined as stated above. The stated release values are the mean from n=3 tests (FIG. 8).

| Time in min | Proportion released in % after treatment for 2 hours at 60° C. | Proportion released in % after treatment for 27 hours at 60° C. |
|---|---|---|
| 120 | 26 | 38 |
| 240 | 63 | 91 |
| 360 | 82 | 101 |
| 480 | 92 | 101 |

Example 3

Tramadol HCl pellets having an active substance content of 55 wt. % were produced by aqueous granulation with microcrystalline cellulose and hydroxypropylcellulose with a low degree of substitution, extrusion and subsequent spheronization. The dried pellets having a screened size of 800–1250 μm were then coated by the fluidized bed method at a feed air temperature of 60° C. initially with 0.6 wt. % of a protective coating and with a total coating weight of 15 wt. %, relative to the weight of the pellets provided with protective coating.

The composition of the aqueous coating dispersion for producing a protective coating on 350 g of pellets was:

| | |
|---|---|
| Opadry OY-29020 clear (=hydroxypropyl-methylcellulose and PEG 400; Colorcon) | 1.60 g |
| Micronized talcum | 0.50 g |
| Purified water | 27.9 g |
| Total: | 30.0 g |

The composition of the aqueous coating composition for coating 300 g of pellets provided with protective coating was:

| | |
|---|---|
| Aquacoat ECD 30 (aqueous ethylcellulose dispersion; Colorcon FMC) | 89.0 g |
| Opadry OY-29020 clear | 3.0 g |
| Dibutyl sebacate | 7.6 g |
| Talcum (micronized) | 7.7 g |
| Polysorbate 80 | 0.03 g |
| Silicon emulsion | 0.03 g |
| Purified water | 129.6 g |
| Total: | 237.0 g |

Figure 9:
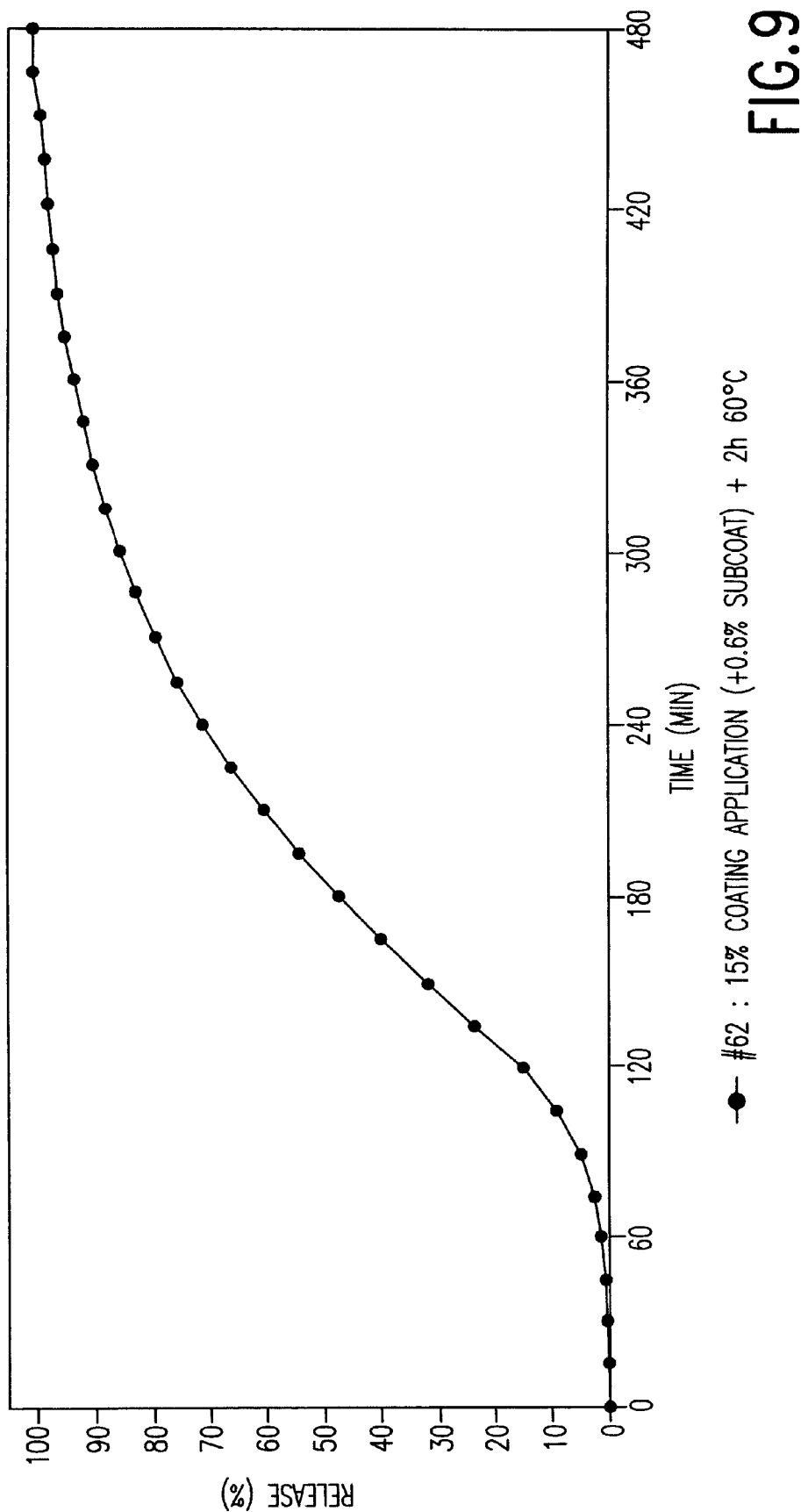
FIG. 9 is a graph showing tramadol release from compression molded tablets containing pellets coated with an Aquacoat ECD 30, Opadry OY-29020 clear (9+1 parts), dibutyl sebacate (25%) and talcum (25%) coating and a 0.6% subcoat.

The solids content of the aqueous dispersion was 19 wt. %. Once the pellets provided with a controlled release coating had been produced, the release profile was adjusted by heat treatment for 2 hours at 60° C. 210 mg of pellets, corresponding to a dose of 100 mg of tramadol hydrochloride were compression molded with 192.1 mg of Cellactose, 16.8 mg of Kollidon CL™ (=Crospovidone) and 1.1 mg of magnesium stearate to form tablets having a diameter of 12 mm and a weight of 420 mg. In water, these broke back down into the individual pellets within 1–2 minutes. Active substance release was determined as stated above. The stated release values are the mean from n=3 tests (FIG. 9).

| Time in min | Proportion released in % (treatment at 60° C., 2 h) |
|---|---|
| 120 | 14 |
| 240 | 70 |
| 360 | 94 |
| 480 | 101 |

Example 4

Tramadol hydrochloride pellets having an active substance content of 33 wt. % were produced by aqueous granulation with microcrystalline cellulose and hydroxypropylcellulose with a low degree of substitution, extrusion and subsequent spheronization. The dried pellets having a screened size of 800–1250 μm were then coated by the fluidized bed method at a feed air temperature of 60° C. with a total coating film weight of 6 wt. %, relative to the starting weight of the uncoated pellets.

The composition of the aqueous dispersion for coating 350 g of pellets was:

| | |
|---|---|
| Aquacoat ECD 30 (aqueous ethylcellulose dispersion; Colorcon) | 58.3 g |
| Dibutyl sebacate | 3.5 g |
| Polysorbate 80 (Tween 80) | 0.01 g |
| Aqueous silicone emulsion | 0.01 g |
| Purified water | 78.2 g |
| Total: | 140.0 g |

An aqueous silicone emulsion was used as an antifoam controller in all the Examples.

Figure 10:
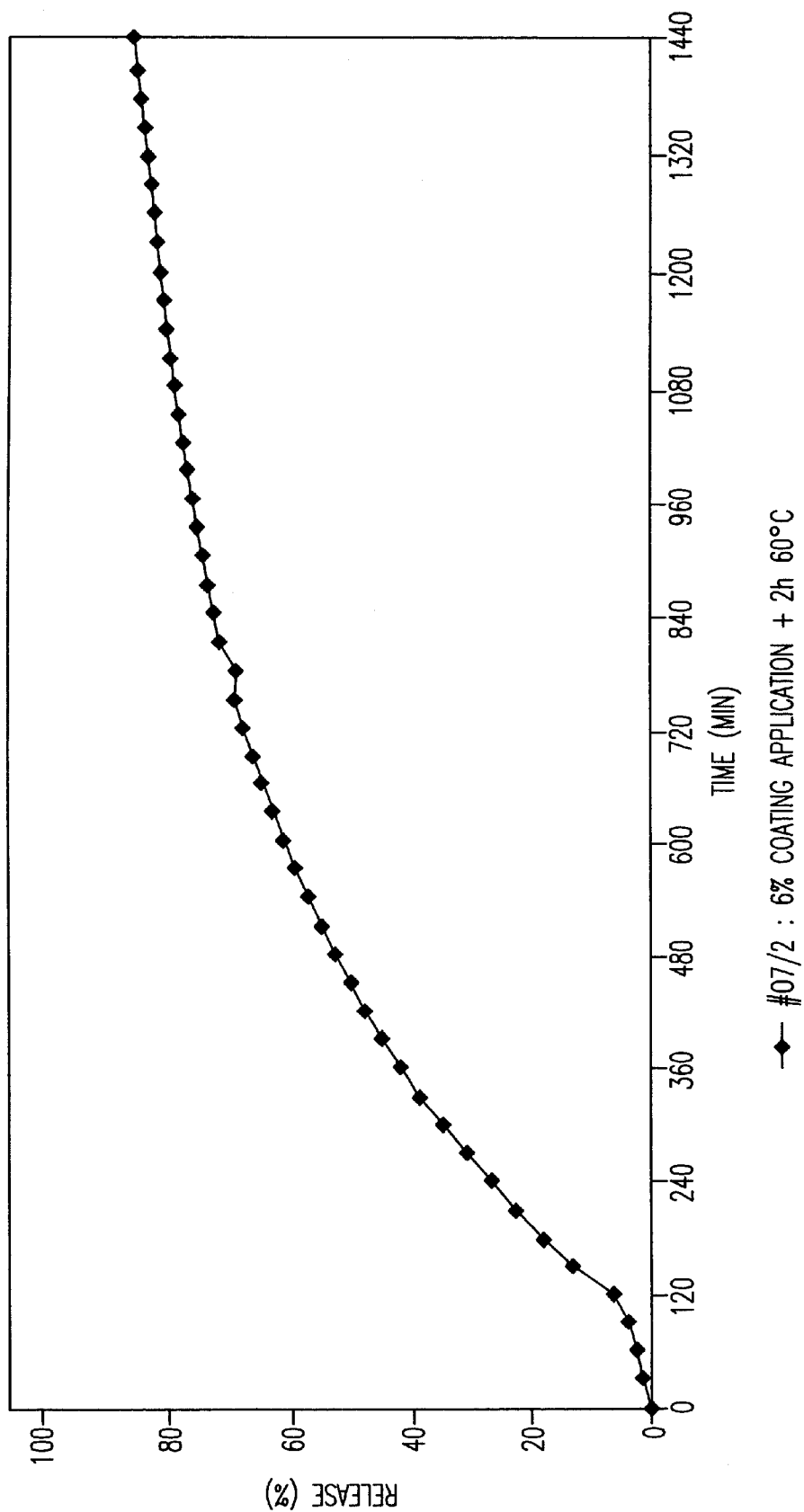
FIG. 10 is a graph showing tramadol release from pellets coated with an Aquacoat ECD 30 and dibutyl sebacate (20%) coating according to the invention.

The solids content of the dispersion was 15 wt. %. Once the pellets had been coated and dried, they were kept at 120° C. for 60 minutes. 321 mg of pellets, corresponding to a dose of 100 mg of tramadol hydrochloride, were packaged in size 0 capsules, and the active substance release was determined therefrom. (FIG. 10).

| Time in min | Proportion released in % |
|---|---|
| 120 | 23 |
| 360 | 36 |
| 600 | 55 |
| 990 | 72 |
| 1440 | 83 |

Example 5

Tablets having a diameter of 10 mm and the following composition were produced on a tabletting press:

| | |
|---|---|
| Tramadol hydrochloride | 100.0 mg |
| Microcrystalline cellulose (Avicel PH 101) | 180.0 mg |
| Polyvidone K30 | 16.0 mg |
| Magnesium stearate | 4.0 mg |
| Total: | 300.0 mg |

Tramadol hydrochloride and microcrystalline cellulose were granulated with an aqueous solution of polyvidone K30, dried, screened and, once mixed with magnesium stearate, compression molded into tablets of a weight of 300 mg. The tablets were coated in a drum coater at a feed air temperature of 60° C. with 5 wt. % of ethylcellulose controlled release film (relative to the weight of the tablets) to yield a tablet weight of 315 mg.

The composition of the coating composition for coating 600 g of tablets was:

| | |
|---|---|
| Surelease E-7-7050 (aqueous ethylcellulose dispersion; Colorcon) | 115.4 g |
| Purified water | 72.1 g |
| Total: | 187.5 g |

Figure 11:
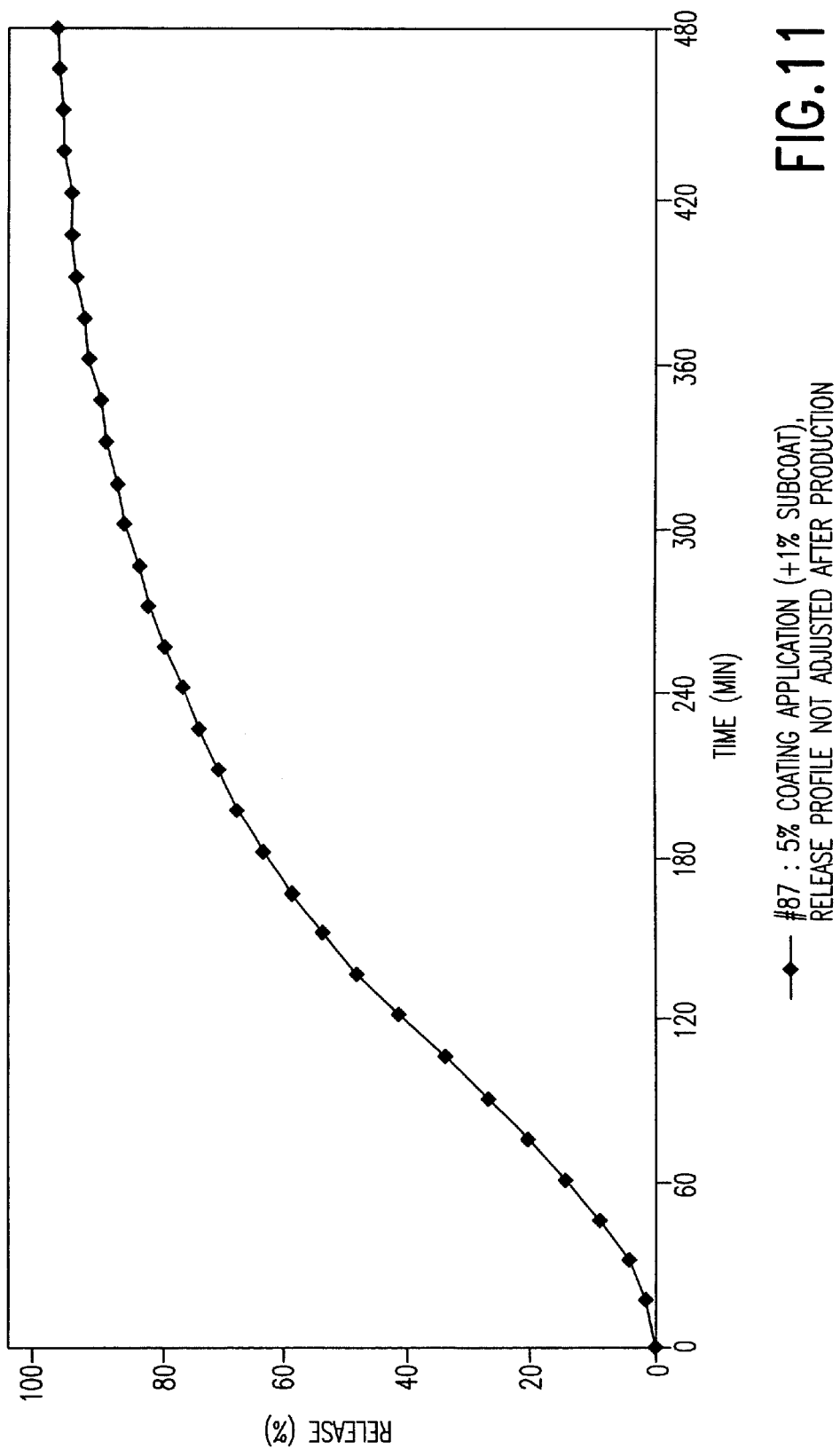
FIG. 11 is a graph showing tramadol release from tablets coated with a 5% Surelease E-7-7050 coating and a 1% subcoat according to the invention.

The solids content of the dispersion was 16 wt. %. No heat treatment was performed after the tablets were coated. The active substance release was determined as stated above. The stated release values are the mean from n=2 tests (FIG. 11).

| Time in min | Proportion released in % |
|---|---|
| 120 | 40 |
| 240 | 76 |
| 360 | 91 |
| 480 | 97 |

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A process for producing an oral, controlled release preparation of tramadol or a physiologically compatible salt of tramadol having a storage stable active substance release profile, said process comprising the step of coating a tramadol or physiologically compatible tramadol salt preparation with an aqueous ethylcellulose dispersion containing at least one physiologically compatible plasticizer comprising a lipophilic diester of a $C_6$–$C_{40}$ aliphatic or aromatic dicarboxylic acid and a $C_1$–$C_8$ aliphatic alcohol, and simultaneously drying the coating at a drying temperature of at least 35° C., whereby a storage stable active substance release profile is obtained without subsequent heat treatment.

2. A process according to claim 1, wherein said plasticizer is a diester of an $C_6$–$C_{30}$ aliphatic or aromatic dicarboxylic acid and a $C_2$–$C_6$ aliphatic alcohol.

3. A process according to claim 2, wherein said plasticizer is a diester of a $C_{10}$–$C_{16}$ aliphatic or aromatic dicarboxylic acid and a $C_2$–$C_5$ aliphatic alcohol.

4. A process according to claim 3, wherein, said plasticizer is selected from the group consisting of dibutyl phthalate, diethyl phthalate, dibutyl sebacate, and diethyl sebacate.

5. A process according to claim 3, wherein said plasticizer is dibutyl sebacate.

6. A process according to claim 1, wherein the plasticizer is used in an amount equal to 5 to 50 wt. % of the ethylcellulose.

7. A process according to claim 6, wherein the plasticizer is used in an amount equal to 10 to 40 wt. % of the ethylcellulose.

8. A process according to claim 7, wherein the plasticizer is used in an amount equal to 10 to 30 wt. % of the ethylcellulose.

9. A process according to claim 1, wherein the ethylcellulose dispersion has an ethylcellulose concentration of from 3 wt. % to 35 wt. %.

10. A process according to claim 9, wherein the ethylcellulose dispersion has an ethylcellulose concentration of from 10 wt. % to 30 wt. %.

11. The process according to claim 1, wherein the drying temperature is between 35° C. and 80° C.

12. A process according to claim 1, further comprising the step of applying a protective coating of water-soluble polymer and talcum prior to coating with the controlled release coating.

13. A process according to claim 12, wherein said water-soluble polymer is hydroxypropylmethylcellulose or hydroxypropylcellulose.

14. A process according to claim 12, wherein the protective coating produces an increase in weight of 1 to 10 wt. %.

15. A process according to claim 14, wherein the protective coating produces an increase in weight of 2.5 to 5 wt. %.

16. A process according to claim 1, wherein said preparation is a tramadol hydrochloride preparation.

17. A process according to claim 1, wherein said tramadol or physiologically compatible tramadol salt preparation is a multiparticulate preparation.

18. A process according to claim 17, wherein said multiparticulate preparation is comprised of microtablets, granules, pellets or crystals.

19. A process according to claim 17, wherein the multiparticulate preparation is comprised of particles having an average particle size of 0.3 to 2.5 mm.

20. An oral, controlled release active substance preparation having a storage stable active substance release profile, wherein said active substance is tramadol or a physiologically compatible salt of tramadol, said active substance preparation being coated with a coalesced ethylcellulose coating obtained by coating a substrate containing the active substance with an aqueous ethylcellulose dispersion containing a plasticizer comprised of a lipophilic diester of a $C_6$–$C_{40}$ aliphatic or aromatic dicarboxylic acid and a $C_1$–$C_8$ aliphatic alcohol, and only drying the coating simultaneously at a drying temperature of at least 35° C., whereby a storage stable active substance release profile is obtained.

21. A controlled release preparation according to claim 20, wherein said preparation is a multiparticulate preparation.

22. A controlled release preparation according to claim 21, wherein said multiparticulate preparation is in the form of microtablets, granules, pellets or crystals.

23. A process according to claim 1, wherein the storage stable active substance release profile remains unchanged at storage conditions of 25–30° C.

24. The process according to claim 11, wherein the drying temperature is between 40° C. and 45° C.

25. The preparation of claim 20, wherein the drying temperature is between 35° C. and 80° C.

26. The preparation of claim 25, wherein the drying temperature is between 40° C. and 45° C.

* * * * *